United States Patent [19]

Pluim, Jr.

[11] Patent Number: 4,594,239

[45] Date of Patent: Jun. 10, 1986

[54] METHOD FOR NEUTRALIZING OFFENSIVE CHEMICALS

[76] Inventor: Arthur W. Pluim, Jr., 602 W. Hickory, Stillwater, Minn. 55082

[21] Appl. No.: 589,595

[22] Filed: Mar. 14, 1984

[51] Int. Cl.$^4$ .............................................. A61K 7/135
[52] U.S. Cl. ........................................ 424/10; 424/62; 252/186.35; 252/187.26; 252/187.34; 514/245; 514/263; 514/289; 514/602; 514/425; 514/805; 422/5
[58] Field of Search ................ 422/5; 424/62, 65, 76, 424/249, 10; 252/187.1, 187.26, 187.33, 187.34, 186.35; 514/245, 263, 289, 602, 425, 805

[56] References Cited

U.S. PATENT DOCUMENTS

| | | | |
|---|---|---|---|
| 2,630,399 | 5/1953 | Sulzberger et al. | 514/392 |
| 2,725,335 | 11/1955 | Lazier | 424/10 |
| 2,885,305 | 5/1959 | Speck | 424/27 |
| 3,003,971 | 10/1961 | Prichard | 548/304 |
| 3,749,772 | 7/1973 | Cardelli et al. | 424/81 |
| 3,756,976 | 9/1973 | Uraneck | 524/836 |
| 3,930,005 | 12/1975 | Wojnar et al. | 424/253 |
| 4,259,318 | 3/1981 | Duhe et al. | 424/94 |
| 4,283,373 | 8/1981 | Frech et al. | 423/226 |

*Primary Examiner*—David L. Lacey
*Assistant Examiner*—Titus B. Ledbetter, Jr.
*Attorney, Agent, or Firm*—Dean P. Edmundson

[57] ABSTRACT

A technique is described for neutralizing unishiol. The technique involves contacting urushiol with a chlorine-containing compound in a liquid medium. In one embodiment the chlorine-containing compound is sodium or calcium hypochlorite in an aqueous solution. In another embodiment the chlorine-containing compound is a chloramine in a liquid organic medium.

11 Claims, No Drawings

METHOD FOR NEUTRALIZING OFFENSIVE CHEMICALS

FIELD OF THE INVENTION

This invention relates to methods and techniques for neutralizing or detoxifying offensive chemicals. More particularly, this invention relates to neutralizing of the toxin urushiol which is present in members of the botanical family Anacardiaceae (e.g., poison ivy, poison oak, poison sumac, cashew, etc.) In another aspect this invention relates to deodorizing of low molecular weight thiols.

BACKGROUND OF THE INVENTION

The irritating nature of poison ivy sap was first recorded in 1609 by Captain John Smith after his arrival in North America. Since that time many compounds and practices have been tried unsuccessfully to mitigate, render harmless, or destroy, the toxic principle of the dermatogenic members of the botanical family Anacardiaceae. The members, which include poison ivy, poison oak, poison sumac, the lacquer tree, mango and cashew, belong to an immunologic cross reacting group which have biochemically similar antigens. The antigens are 1,2 dihydroxy-benzenes with a 15 or 17 carbon atom aliphatic side chain which has varying degrees of unsaturation. It is not unusual for the sap of different plants to have mixtures of dihydroxy benzenes or to have these compounds in common but at different concentration levels.

The allergic contact dermatitis is reported in the literature to be caused by the catechol moiety as the primary allergen. The aliphatic hydrocarbon side group allows bonding to and penetration of the skin.

Exposure of skin to the urushiol, after a time, results in a painful rash and itching at the area of contact which often proceeds to vesicles. The dermatological reaction may require a month or more to heal.

Bare skin contact with the urushiol is a prerequisite for the allergic reaction. However, direct contact with the plant sap by bare skin is not necessary and often is not the primary contamination surface. In fact, there are many vectors responsible for the spread of the urushiol; for example, clothing, tools, and domestic animals, and even the fingers spread the urushiol to other parts of the body. Failure to appreciate an exposed article as a carrier is responsible for most personal exposure. Evading this secondary contamination from exposed articles is difficult because of the small amount of the urushiol needed to cause the allergic reaction as well as the relatively unobtrusive evidence of its presence. Furthermore, even if exposure of skin or articles were noted, this most often would occur in the field where there is usually no access to relief, such as clean clothes or the ability to scrub with soap and water. Additionally, contaminated articles can retain allergic reaction-causing capabilities for up to one year after the original exposure because of the refractory nature of the urushiol oleoresin.

It might seem relatively easy to destroy the urushiol since the catechol moiety is a strong reducing agent and might be expected to react readily with strong oxidizing agents to accomplish its destruction. This is the case when acidic, aqueous solutions of strong oxidizers such as permanganates, peroxides, or chlorites effectively destroy the catechol as the water soluble pyrocatechol. However, these same oxidizing agents will not destroy the hydrophobic catechol moiety as presented in the urushiol.

SUMMARY OF THE INVENTION

In accordance with the present invention techniques are described for effectively neutralizing urushiol on a surface (e.g., wearing apparel, skin, tools, pets, etc.) The techniques include contacting the urushiol with a solution comprising a chlorine-containing compound which is capable of reacting with urushiol to produce non-allergic reaction products.

Using the techniques of this invention, urushiol on exposed surfaces is destroyed so that secondary contamination is avoided quickly and efficiently.

In another aspect of the invention it has been found that the chlorine-containing compounds are also effective in deodorizing low molecular weight thiols such as are present in skunk spray or glandular secretions of other small animals. Thus, the technique is effective for eliminating the offensive odor of skunk spray, etc. from wearing apparel, pets, and so forth.

DETAILED DESCRIPTION OF THE INVENTION

In the description of this invention the term "urushiol" is used to generically include any dermatogenic 1,2-dihydroxy benzene with a 15 or 17 carbon atom side chain in the 3 position on the benzene ring. The reference herein to a "surface" refers normally to the upper or exterior bounds of an object which may have come into contact with the sap and toxic principle of the dermatogenic members of the botanical family Anacardiaceae. Examples of such surfaces include wearing apparel (e.g., clothing, shoes, boots), skin, animal hair, tools, toys, etc.

The chlorine-containing compounds which have been found useful in the techniques of this invention may be inorganic or organic. Suitable inorganic compounds include chlorine-oxygen acids, or salts thereof, and chlorine dioxide, in aqueous solution. Representative useful inorganic compounds include, for example, sodium, potassium or calcium hypochlorites, chlorites, chlorates, and perchlorates. Another class of chlorine-containing compounds which are useful in this invention are chloramines (in liquid organic media).

Thus, these compounds are effective in destroying or neutralizing urushiol on exposed surfaces (e.g., wearing apparel, tools, etc.). In this manner secondary exposure to urushiol contact is eliminated or avoided. These compounds are also effective in neutralizing (i.e., deodorizing) low molecular weight thiols such as are present in skunk spray and in glandular secretions of other small animals such as cats, ferrets, and so forth.

The aqueous solutions of the inorganic chlorine-containing compounds preferably have a concentration of about 2% to 6% by weight. Below a concentration of about 2% the solution does not always neutralize all of the urushiol or low molecular weight thiol. Above about 6% concentration no additional efficacy is observed. The aqueous solutions are particularly useful for treatment of surfaces which might be adversely affected by organic solvents. The alkali typically used to stabilize hypochlorite solutions also serves as an indicator which shows the presence of urushiol by producing a green color which fades coincident with the destruction of the urushiol. This alkali is normally sodium or potassium hydroxide.

If desired, there may be added to the aqueous solution a small amount of a primary alcohol (e.g., methyl alcohol, ethyl alcohol, isopropyl alcohol) as a wetting agent in order to enhance the action of the hypochlorite solution. The amount of alcohol added is typically in the range of about 5 to 20 volume percent.

Although the aqueous hypochlorite solutions are useful in the practice of this invention they are not preferred. They may take approximately five minutes to neutralize urushiol, may have difficulty in neutralizing large concentrations of urushiol, and do have difficulty with urushiol which has aged on a surface for several days. These solutions also can tend to bleach clothing being treated.

The preferred chlorine-containing compounds used in the techniques of the present inventions are chloramines, which may be organic or inorganic, which contain one or more chlorine atoms attached to nitrogen. They include: chloramines, chlorimines, chloramides, and chlorimides. Organic chloramines in which the nitrogen to which the chlorine is attached also include one or more organic radicals. Since these radicals may also contain chlorine, the organic chloramines are termed N-chloramines.

The inorganic members of the class of substituted chloramines, e.g., monochloramine, nitrogen trichloride, N-chlorosulfamic acid, etc. are unstable and are of theoretical interest.

The N-chloramines have been previously used in aqueous solution for sanitation of water and dairy equipment. They are also used for household and commercial bleaches, scouring powders, and dishwashing compounds. The chloroisocyanurics, glycolurils, chlorinated hydantoins, chloramine-T, N-chlorosuccinimide, and trichloromelamines are examples of such N-chloramines. N-chlorosulfonamides are also useful N-chloramines.

Tri- and di-chloroisocyanuric acids, 1,3-dichloro-5,5-dimethyl hydantoin, and chloramine-B are N-chloramines which have good solubility in organic solvents and accordingly provide particular utility in the techniques of the present invention. During the World War II era the N-chloramines in organic solvents were used for decontamination of structures and clothing exposed to mustard gas. A number of U.S. Patents refer to clothing impregnation and protective gels or ointments for use against chemical warfare agents: U.S. Pat. Nos. 2,638,434; 3,649,389; 2,725,335; 2,885,305; 3,002,975; and 3,003,971.

In the present invention, trichloroisocyanuric acid (also known as chlorinated s-triazine trione) has been found particularly useful for neutralizing or destroying the urushiol. This acid is particularly unique because it is not useful in aqueous media but it is extremely effective in organic solvent media.

The preferred organic solvents are ketones such as acetone or methyl ethyl ketone; acetates such as ethyl or butyl, or chlorinated solvents such as methylene chloride or ethylene chloride. These solvents may be used alone or in combination, or in combination with smaller amounts of other solvents (even including water) to control evaporation rate, wetting of substrates, or flammability characteristics. Examples of such additional solvents are methyl, ethyl, isopropyl alcohol, aliphatic hydrocarbons such as heptane and hexane, and acetone alcohol.

The use of organic solvents is particularly beneficial for other reasons also: surfaces to be treated are wet quickly because of lower surface tension; and the solvent solutions spreads quickly over and through a substrate, thereby lessening the criticality of application of the solution to the contaminated surface.

A typical, preferred formulation for use in the present invention is as follows:
Acetone: 12.6 parts by weight
Butyl acetate: 1.3 parts by weight
TCIA*: 0.7 part by weight
*Trichloroisocyanuric acid, commercially available as ACL 90+ from Monsanto.

This formulation destroys the urushiol on a surface in less than one minute, dries in two minutes and does no damage to cloth fibers or colors of easily bleached fabrics.

The useful concentration range of the active decontaminating agent is between 0.5 and 5% by weight in solution. Below 0.5%, the ability to handle the occasional large concentration of the urushiol is poor; whereas above 5% concentration no advantage is offered in efficacy. The preferred concentration range of active ingredient is 1-2% by weight of total solution. It has also been discovered that dispersions as well as true solutions of trichloroisocyanuric acid destroys the urushiol. A dispersion of 5% by weight in a mixture of 50:50 ethylene chloride and methyl ethyl ketone works effectively.

The stronger solutions of trichloroisocyanuric acid (greater than 2%) in organic solvent were found not to bleach colors. However, upon drying, some of the solid trichloroisocyanuric acid remains on the surface which when contacted with water results in color bleaching. If it is desirable to use these stronger solutions advantage can be taken of the non-aqueous medium to counteract the bleaching effect. A water soluble or hydrolyzable means of supplying an alkali is dissolved or dispersed in the organic solvent along with the trichloroisocyanuric acid. They will not react in this environment. Upon contact with water, however, the alkali and the trichloroisocyanuric acid react, removing the bleaching hazard by deactivating the acid. Sodium or potassium bicarbonate, sodium or potassium hydroxide, and methoxides (e.g., sodium methoxide) are preferred examples of compounds useful for limiting the bleaching activity of the trichloroisocyanuric acid. Carbonates such as sodium and potassium are also useful.

Additionally, a means of indicating the presence and subsequent destruction of the urushiol can be employed by dissolving a ferric salt in the organic solvent solution containing the trichloroisocyanuric acid. Such ferric salts include, for example, ferric nitrate, ferric chloride, ferric ammonium citrate or ferric acetate.

Because of the uncertainty of storage conditions prior to sale of the composition to the ultimate consumer, and in order to obtain a maximum storage life, it is preferred to package the trichloroisocyanuric acid and its solvent system separately. It is also preferred to package the dry powder and the solvents in such a manner that they can be brought together easily for use. The trichloroisocyanuric acid powder can be supplied as a pellet or tablet, or any other means of supplying a premeasured dose. Then the pellet or tablet may be combined with the solvent system when the treating solution is needed. Other means of packaging and using the compositions may also be used. For example, the chlorine-containing compound may be included in a sponge or other porous medium which may be adapted to be attached to the opening of the container for the solvent in a manner such that the dispensed solvent passes through the sponge or porous medium and dissolves the chlorine-containing compound. For example, the sponge or other porous medium may be attached to a threaded connection means which is adapted to be threadably secured to the opening of the container holding the solvent.

The preferred manner, however, is to package the trichloroisocyanuric acid in a mesh bag constructed of a non-woven polypropylene fabric such as "Celestra," commercially available from Crown-Zellerbach Company. This mesh bag containing the powder can optionally be attached to the stem of a spray head. These items, (the bottle with the solvent system and the spray head with the mesh bag attached) are packaged separately. When it is desirable to use the decontaminating means, the pump is introduced into the bottle containing the solvents. The solvents then dissolve the trichloroisocyanuric acid from the mesh bag and the solution is ready for use. This system has the additional advantage in that personal access to the active ingredient is greatly restricted (unlike a pill or tablet which might easily be ingested). This means of packaging provides a long storage life for the product.

When human or animal skin is the primary surface which has been contacted by urushiol there is a time constraint in which to neutralize or destroy the urushiol. After initial skin contact by urushiol there is an induction period of 15-30 minutes. If the exposed skin surface is cleansed or treated during the induction period to remove or destroy the urushiol, then the typical allergic response is averted. Consequently, the chemical cleansing or decontamination should work quickly, preferably in less than 5 minutes. Also, since the decontamination means is being applied directly to the skin, a low order of dermal toxicity is required. Both the hypochlorites and chloroisocyanurates exhibit low dermal response. This allows their use on pets and other domestic animals which are sometimes carriers of urushiol contamination.

An example of the use of the chemical decontamination means on the human skin is as follows: Zones, approximately 2.5 cm in diameter, are marked on the forearm of a human subject. Each zone is treated with 2-5 drops of a 1½% catechol solution in water. At intervals of 5, 10, 15, 20, and 30 minutes, different zones are treated with a 5.25% stabilized sodium hypochlorite aqueous solution. A control zone is left untreated. After removing excess fluid with a paper towel, the sites are left undisturbed for 2 minutes. At that time a pad saturated with 20% by weight ferric nitrate aqueous solution is daubed across the experimental area and reactions are observed. The control zone turns black from the catechol-ferric ion reaction. The zones treated with the hypochlorite solution show various responses: the zones treated at the 5 and 10 minutes intervals do not show any black color indicative of contact appearing as undisturbed skin; the zone treated at the 15 minute interval has a slight bit of color indicative of some binding to the skin. The sites treated at the 20 and 30 minute intervals are only slightly less dark than the control zone. No reddening or other sign of skin irritation is noted. Thus, the decontamination means is operable within the required time frame.

The compositions useful in the present invention can be delivered to the desired surface to be decontaminated by any practical means including but not limited to aerosol sprays, pump sprays, wipes, swabs, immersion, sprinkling and the like. Thus, the present invention comprises a chemical means for deactivating, destroying or otherwise rendering harmless the toxic principle, urushiol, found in the sap of poison ivy, poison oak, poison sumac and related plants of the botanical family Anacardiaceae, on surfaces exposed to same. It comprises a chlorine containing compound in a suitable carrier. This means is operable on surfaces as exposed, and in the field environment if necessary.

In another aspect the present invention provides means for deodorizing low molecular weight thiols, such as those present in skunk spray and in glandular secretions of other small animals such as cats, ferrets, etc. Exposure to skunk spray is a great annoyance because of its very disagreeable and persistent odor due to the low molecular weight thiols. The odor may persist for several days on anything contacted by the spray, e.g., wearing apparel, pets, articles, etc. In particular, dogs are often exposed to the spray and become a nuisance when attempts are made to decontaminate them, restrain them, etc.

Because the skunk spray is quite hydrophobic, removal of the spray and the primary odor-causing factors (n-butanethiol and 2-methylbutanethiol) by ordinary means such as soap and water is very difficult. Soaking exposed articles in tomato juice or perfumed detergents for extended periods have been suggested but have not proven effective.

It has also been suggested that thiols can be deodorized by oxidizing them to the disulfides. This is common practice in the sweetening of sour natural gas. However, such processes involve the use of catalysts and high temperatures and are performed in continuous flow reactors under controlled conditions.

It has been found that the compositions described above in connection with the neutralization of urushiol also have utility in oxidizing low molecular weight thiols to thereby deodorize them. The compositions described above are effective in deodorizing the thiols despite the hydrophobic nature thereof.

The use of the N-chloramines such as trichloroisocyanuric acid are preferred for use on clothing and pets. The solvent systems used for the N-chloramines may be adjusted to provide desired evaporation rates and solvency for the thiol/carrier mixture. The solvent combinations described above are useful, with particular emphasis on solvents known to be good solvents for fatty and oily substances.

Effectiveness of hypochlorite and N-chloramine in deodorizing thiols was demonstrated as follows: Three vials were prepared and identified as:

A—5 ml. of sodium hypochlorite (5.25% by weight in water)

B—5 ml. of "Skunk-Off", a commercially available perfumed detergent in water

C—5 ml. of trichloroisocyanuric acid (3% by weight in acetone, methyl alcohol, and hexane)

To each of the vials was added 2 ml. of "Buck Stop Skunk Scent," commercially available from Buck Stop Lure Company. It contains extract of skunk scent gland in a fatty base with a consistency similar to heavy cream. It exhibits a very heavy skunk odor.

Each vial is then capped and shaken. The results were as follows:

A—strong foaming reaction; upon opening of the vial there was a strong chlorine smell but no skunk odor B—immediate dispersal of the material; upon opening of the vial there was a very strong skunk odor C—no reaction observed; upon opening of the vial it was almost odorless with only a faint ammonia smell The compositions of the invention are also useful in the deodorizing of similar thiols such as methanethiol, ethanethiol, 1-propanethiol, 2-propanethiol, 2-methyl-1-propanethiol, 2-methyl-2-propanethiol, and the like. The compositions may be delivered in the same manner as described above in connection with their use for neutralizing urushiol.

Other variants of the invention are also possible without departing from the scope and spirit of the present invention.

What is claimed is:

1. A method for decontaminating a surface which has been exposed to urushiol, said method being for the purpose of neutralizing said urushiol, wherein said method comprises contacting said urushiol with an effective amount of a solution of a chlorine-containing compound which is capable of reacting with urushiol to produce non-allergenic reaction products, wherein said solution is selected from the group consisting of:
   (a) an aqueous solution of sodium or calcium hypochlorite further containing an alkali selected from the group consisting of carbonates, bicarbonates, hydroxides, and methoxides; and
   (b) an N-chloramine in a liquid organic medium selected from the group consisting of ketones, acetates, and chlorinated solvents.

2. A method in accordance with said 1, wherein said surface comprises wearing apparel.

3. A method in accordance with claim 1, wherein the solution is the N-chloramine in said liquid organic medium and the concentration of N-chloramine in said medium is between about 0.5 to 5% by weight.

4. A method in accordance with claim 1, wherein said solution is the N-chloramine in said liquid organic medium, the N-chloramine comprises trichloroisocyanuric acid and said organic medium comprises acetone and butyl acetate.

5. A method in accordance with claim 1, wherein said solution further comprises a solution modifier selected from the group consisting of low molecular weight alcohols, aliphatic hydrocarbons, acetone alcohol and water.

6. A method in accordance with claim 1, wherein said solution of a chlorine containing compound is applied to said surface by spraying, wiping, or immersion.

7. A method in accordance with claim 1, wherein said solution is the N-chloramine in the liquid organic medium and the N-chloramine is selected from the group consisting of chloroisocyanurics, chlorinated hydantions, chloramine-T, N-chlorosuccinimide, trichloromelamines, and N-chlorosulfonamides.

8. A method in accordance with claim 1, wherein said N-chloramine is selected from the group consisting of trichloroisocyanuric acid, dichloroisocyanuric acid, 1,3-dichloro-5,5-dimethyl hydantoin, and chloramine-B.

9. A method in accordance with claim 1, wherein said solution further comprises indicator means for indicating the presence of urushiol.

10. A method in accordance with claim 9, wherein said indicator means comprises an alkali selected from the group consisting of sodium and potassium hydroxides and carbonates.

11. A method in accordance with claim 9, wherein said indicator means is selected from the group consisting of ferric nitrate, ferric ammonium citrate, ferric chloride and ferric acetate.

* * * * *